(12) United States Patent
Wessel

(10) Patent No.: US 9,107,889 B2
(45) Date of Patent: Aug. 18, 2015

(54) COMPOSITIONS COMPRISING AN NO DONOR AND A DITHIOLANE AND THEIR USE FOR IMPROVEMENT OF SEXUAL FUNCTION

(75) Inventor: Klaus Wessel, Bad Vilbel (DE)

(73) Assignee: Encrypta GmbH, Bad Homburg (DE)

( * ) Notice: Subject to any disclaimer, the term of this patent is extended or adjusted under 35 U.S.C. 154(b) by 341 days.

(21) Appl. No.: 11/568,283

(22) PCT Filed: Aug. 4, 2006

(86) PCT No.: PCT/EP2006/007733
§ 371 (c)(1),
(2), (4) Date: Oct. 25, 2006

(87) PCT Pub. No.: WO2007/017191
PCT Pub. Date: Feb. 15, 2007

(65) Prior Publication Data
US 2008/0161381 A1   Jul. 3, 2008

(30) Foreign Application Priority Data

Aug. 4, 2005 (EP) .................................. 05107206

(51) Int. Cl.
*A61K 31/198* (2006.01)
*A61K 31/385* (2006.01)

(52) U.S. Cl.
CPC .............. *A61K 31/198* (2013.01); *A61K 31/385* (2013.01)

(58) Field of Classification Search
CPC ..................................................... A61K 31/198
See application file for complete search history.

(56) References Cited

U.S. PATENT DOCUMENTS

| 4,772,727 | A  | * | 9/1988 | Sutherland et al. | ............. 549/39 |
| 5,281,722 | A  |   | 1/1994 | Blaschke et al. | |
| 6,207,190 | B1 | * | 3/2001 | Richardson et al. | .......... 424/472 |
| 6,387,645 | B1 |   | 5/2002 | Ford et al. | |
| 6,387,945 | B2 |   | 5/2002 | Packer et al. | |
| 6,605,637 | B1 |   | 8/2003 | Harnett et al. | |
| 2002/0006907 | A1 | | 1/2002 | Gardiner et al. | |
| 2002/0068365 | A1 | * | 6/2002 | Kuhrts | .......................... 436/501 |

FOREIGN PATENT DOCUMENTS

| CN | 1429113 A | 7/2003 |
| DE | 3840076 A1 | 6/1989 |
| DE | 4035442 | 5/1991 |
| DE | 4317646 | 12/1994 |
| EP | 089126 | 9/1983 |
| EP | 0318891 A1 | 6/1989 |
| EP | 947194 | 10/1999 |
| EP | 1273295 | 1/2003 |
| IE | 88/3618 B1 | 8/1994 |
| WO | 00/59442 | 10/2000 |
| WO | WO-01/85178 A1 | 11/2001 |
| WO | WO-02/19999 A | 3/2002 |
| WO | WO-03/028714 A | 4/2003 |
| WO | WO-03/032751 A | 4/2003 |
| WO | WO 03/084532 A1 | * 10/2003 | ........... A61K 31/385 |
| WO | WO-2003/084532 A1 | 10/2003 |
| WO | WO-2007/017191 A2 | 2/2007 |

OTHER PUBLICATIONS

Hurdag C, Ozkara H, Citci S, Uyaner I, Demirci C. The effects of alpha-lipoic acid on nitric oxide synthetase dispersion in penile function in streptozotocin-induced diabetic rats. Int J Tissue React. Feb. 2005;27(3):145-50.*
Wordnet Search 3.1. wordnetweb.princeton.edu.*
Hurdag citation page, ResearchGate.net. Feb. 2005.*
Maas R, Schwedhelm E, Albsmeier J, Böger RH. The pathophysiology of erectile dysfunction related to endothelial dysfunction and mediators of vascular function. Vasc Med. Aug. 2002;7(3):213-25.*
Biewenga, G.P. et al: "The Pharmacology of the Antioxidant Lipoic Acid" General Pharmacology, Pergamon Press Oxford, GB, vol. 29, No. 3, 1997, pp. 315-331.
European Search Report for European Application No. EP05107206, dated Jan. 10, 2006.
L. Ja. Report "Peculiarities for treating erectile dysfunction in patients suffering from diabetes", Theoretical and practical conference "Sexual culture and sexual health of the nation", May 12, 2002, Found in the Internet on: http://www.mosmedclinic.ru/conf_library/2/25/1999/ (w/English abstract—Computer Translation).
Indrani Maitra et al.; "Stereospecific Effects of R-Lipoic Acid on Buthionine Sulfoximine-Induced Cataract Formation in Newborn Rats"; Biochemical and Biophysical Research Communications, 221, 1996, pp. 422-429.
αJens Lykkesfeldt et al.; "Age-associated decline in ascorbic acid concentration, recycling, and biosynthesis in rat hepatocytes-reversal with (R)-α-lipoic acid supplementation"; The FASEB Journal, vol. 12, Sep. 1998, pp. 1183-1189.
Tory M. Hagen et al.; "(R)-α-Lipoic acid-supplemented old rats have improved mitochondrial function, decreased oxidative damage, and increased metabolic rate"; The FASEB Journal, vol. 13, Feb. 1999, pp. 411-418.
AIN-93M data sheet, 2010, 1 page.

* cited by examiner

*Primary Examiner* — Paul Zarek
(74) *Attorney, Agent, or Firm* — Hudak, Shunk & Farine Co. LPA

(57) ABSTRACT

The present invention relates to solid compositions comprising a substance which improves nitric oxide (NO) availability, re. an NO donor or a precursor of the biosynthesis of nitric oxide or an direct or indirect NO agonist, with arginine being a preferred compound, in combination with a dithiolane, with α-lipoic acid as a preferred compound, and its use for improvement of sexual function. The compositions according to the invention comprise the NO donor or its precursor in excess, based on the molar amount of the constituents. The compositions are also suited for the improvement of sexual function. In particular the present invention relates to the use of a dithiolane in combination with a NO donor or a precursor thereof for the preparation of a medication for treatment of sexual dysfunction.

9 Claims, No Drawings

COMPOSITIONS COMPRISING AN NO DONOR AND A DITHIOLANE AND THEIR USE FOR IMPROVEMENT OF SEXUAL FUNCTION

CROSS-REFERENCE TO PRIOR APPLICATIONS

This is a U.S. National Phase application under 35 U.S.C. §371 of International Application No. PCT/EP2006/007733, filed Aug. 4, 2006, and claims the benefit of European Patent Application No. 05 107 206.4, filed Aug. 4, 2005, both of which are incorporated by reference herein.

The present invention relates to solid compositions comprising a substance which improves nitric oxide (NO) availability, re. an NO donor or a precursor of the biosynthesis of nitric oxide or a direct or indirect NO agonist, with arginine being a preferred compound, in combination with a dithiolane, with α-lipoic acid as a preferred compound, and its use for improvement of sexual function. The compositions according to the invention comprise the NO donor or its precursor in excess, based on the molar amount of the constituents. The compositions are also suited for the improvement of sexual function. In particular the present invention relates to the use of a dithiolane in combination with a NO donor or a precursor thereof for the preparation of a medication for treatment of sexual dysfunction.

Sexual function is a central biological and social factor in the life of an adult human being. It contributes to the quality of a partnership and is a prerequisite to achieve individual reproductive goals. It can compensate external impacts and stress. Intact or positively experienced sexual function thereby has a positive feedback on other organic functions and may ameliorate health in general. Most. people perceive intact sexual life as a key factor for a positive life quality.

Sexual health and sexual function can be impaired in many ways. It can be the absence of libido or the impairment of organic sexual functions. Men and women suffer often in different ways. Nonetheless, available treatments or improvement methods are currently primarily directed and in many cases limited to support male erectile dysfunction (ED).

Since an erection requires a precise sequence of events, ED can occur when any of these events is disrupted. The sequence includes nerve impulses in the brain, spinal column, and area around the penis, and response in muscles, fibrous tissues, veins, and arteries in and near the corpora cavernosa.

Damage to nerves, arteries, smooth muscles, and fibrous tissues, often as a result of disease, is the most common cause of ED. Diseases, such as diabetes, kidney disease, chronic alcoholism, multiple sclerosis, atherosclerosis, vascular disease, and neurological disease, account for physically erectile dysfunction. Between 35 and 50 percent of men with diabetes experience ED.

Also, surgery (especially radical prostate and bladder surgery for cancer) can injure nerves and arteries near the penis, causing ED. Injury to the penis, spinal cord, prostate, bladder, and pelvis can lead to ED by harming nerves, smooth muscles, arteries, and fibrous tissues of the corpora cavernosa.

In addition, many common medicines, as for example blood pressure drugs, antihistamines, antidepressants, tranquilizers, appetite suppressants, and cimetidine (an ulcer drug), can lead to ED as a side effect.

Experts believe that psychological factors such as stress, anxiety, guilt, depression, low self-esteem, and fear of sexual failure also cause ED. Men with a physical cause for ED frequently experience the same sort of psychological reactions (stress, anxiety, guilt, depression).

Other possible causes are smoking, which affects blood flow in veins and arteries, and hormonal abnormalities, such as lack of testosterone.

ED is clinically assessed by the application of the International Index of Erectile Function (IIEF Scale). The scale consists of 5 items related to erectile function scored from never (1 points) to always (5 points). 21-25 points translate to the absence of ED, 16-20 points relate to a mild ED, 11-15 points relate to a moderate ED and 5-10 points translate to a severe ED.

Female sexual function can be assessed by the Index of Female Sexual Function (IFSF), a 9-item self-assessment questionnaire. The IFSF is much more comprehensive in respect of sexual function assessment compared to the IIEF. Parameters to be assessed are discomfort during intercourse, degree of vaginal dryness, number of attempts to intercourse, rate and degree of sexual desire, level of satisfaction with sex life and relationship, degree of clitoral sensation and quality of orgasm.

One prominent current therapy of ED is the application of phosphodiesterase inhibitors of type 5 (PDE5-I) like Silfenadil, Vardenafil or Tadalafil. Due to their mechanism of action, PDE5-I do not induce an erection, they rather improve an erection. However, they can only work in case of sexual excitement, they cannot induce sexual excitation. Due to the mode of action, PDE5-I cannot be used in condition of cardiac or vascular diseases. Particularly, they can cause deadly side effects when taken together with nitrate medications. They can also not be taken together with sexual stimulations like NO-donors (as for example alkylnitrates and -nitrites).

Other medications with different modes of action but similar limits are apomorphine and yohimbine. A local medication is prostaglandin E1 (Alprostadil), which has to be injected in the penis and can induce an erection. Such treatment, however, is not convenient to the patient at all.

The before mentioned medications will help to improve or induce erection. None of these medications ameliorates other signs and symptoms of sexual function, particularly absence of libido or premature ejaculation and they do not help women. The even do not help in cases of psychogenic ED.

α-lipoic acid is known in medical, nutritional and pharmaceutical use since decades. Its use has been proposed either as racemic mixture, as one of the enantiomers or mixtures of the enantiomers (DE 4035442A1). It has also been proposed to modify it chemically (for example: to the reduced dithiol, liponamide and its derivates as described in U.S. Pat. No. 6,387,945B2, β-lipoic acid, methyllipoic acid, bis- and tetratnorlipoic acid, thiosulfonates, silfinyl sulfones, disulfones, sulfonic acid and other derivatives as described in EP 089126 A1, ester-coupled to glycerine, esters and amides and salts in general and others). The use of salts and metabolites has been suggested as well. The redox site of a dithiolane group with a redox potential of −0.325 volts is the active moiety of all of these chemical modifications. Thereby, the dithiolane moiety reduces all intracellular redox systems and can be recycled enzymatically and non-enzymatically by NADH- and NADPH redox equivalents. The molecular derivatives of the dithiolane moiety all depend pharmacodynamically on this basic mechanism. However, chemical derivatisation influences metabolism, distribution and the turnover rate of redox recycling.

Preparations include tablets, capsules, ampoules for infusion, ready-to-use infusions and preparations for transdermal, subcutaneous and rectal application, as well as formulations for inhalation, alone and in combinations. Quick release, controlled release and slow release formulations are described. According to the literature, the compound is suggested for various states and diseases, such as for example diabetic polyneuropathy, liver disease, mushroom poisoning, heavy metal intoxications, radiation disease, diabetes, hyperlipidaemia, skin disorders, migraine etc. Also combined uses with acetylcholinesterase inhibitors in Alzheimer's disease, and other conditions are suggested.

The compound arginine is used in situations of transient fatigue and has been proposed to normalize low density cholesterol after chronic intake. Still further, it has been proposed to be used in erectile dysfunction since it is a precursor for NO synthesis. It is assumed that NO improves penile circulation and thereby improves erectile tension. Such an assumption, however, has not yet been confirmed clinically. However, there are proposals to combine NO donor compounds or NO agonistic compounds like arginine with PDE5-inhibitors to treat erectile dysfunction.

One modulator of vascular relaxation is nitric oxide (NO), the so-called endothelial derived relaxing factor. As a very general assumption all antioxidants, i.e. also dithiolanes like α-lipoic acid, were proposed to have a positive effect on the availability of nitric oxide (NO). In the test tube, one of the reactive oxygen species, superoxide anions, reacts with NO to form peroxynitrite (Du et al.). An antioxidant like α-lipoic acid scavenges free oxygen radicals and would thereby increase the bioavailability of NO. However, according to other data from cellular test systems, this proposed mechanism to potentially increase NO availability was disproved. Liang and Akaike reported that α-lipoic acid inhibited NO synthesis in hepatocytes, cytokine-induced NO-formation was reduced by thiols including α-lipoic acid (Tabatabaie et al.) and NO-production due to proinflammatory stimulation (Guo et al.). In conclusion, thiols including α-lipoic acid were shown to decrease the activity of nitric oxide synthase (NOS). Therefore, derivates of α-lipoic acid have even been developed for the use as NO-synthase inhibitors (U.S. Pat. No. 6,605,637; US 2004/00190084 A1). Furthermore, other inhibitors of nitric oxide synthase and NO synthesis like nitro-arginine have been proposed to be combined with thiols inclusive α-lipoic acid (WO 03/028714 A2; WO 00/59448) due to the same direction of the pharmacological action.

In conclusion, no rationale for a stimulatory in-vivo effect of α-lipoic acid and dithiolanes on NO bioavailability can be formulated. In contrast, an inhibitory action is the state of the art. Therefore, hitherto no report exists to apply arginine and α-lipoic acid together or a composition of both to improve conditions of erectile dysfunction and no test results have been reported on a additive or synergistic effect of both components on NO bioavailability. The only proposal to combine both compounds in conditions of erectile dysfunction is to reduce arginine-dependent side effects (generation of free oxygen radicals) by an antioxidant and is directed to the simultaneous application with carnitine and coenzyme $Q_{10}$ (WO 03/032751).

Particularly, it is not mentioned in the literature to apply arginine and α-lipoic acid together to improve sexual function in general, inclusive functions that do not depend on nitric oxide. In contrast, antioxidant combinations including α-lipoic acid have only been proposed to scavenge oxygen free radicals appearing due to arginine supplementation, as stated in WO 03/028714, with the goal to prevent arginine-dependent side effects like pulmonary toxicity.

WO 03/032751A1 describes the use of a salt of carnitine and zinc chloride plus a solid mixture of arginine, coenzyme $Q_{10}$ and α-lipoic acid in ratios of 1-3 g, 80-100 mg and 20-50 mg in sexual disorders in men (sperm mobility and erectile dysfunction). $Q_{10}$ and α-lipoic acid were added to reduce side-effects of arginine (free radical production), not to improve the pharmacodynamic action or to add pharmacodynamic actions.

Combinations of ozonized oils with α-lipoic acid and arginine have been described with a maximum amount of 25% by mass of arginine in EP 1 273 295 A1). EP 947 194 B1 describes the mixture of arginine with α-lipoic acid, with both forming a solid salt. The salt formation between α-lipoic acid and alkaline amino acids has also been described for liquid compositions for injection and infusion, as described in DE 3840076A1. Some patent documents, as U.S. Pat. No. 5,281,722, refer to the separation of the enantiomers of α-lipoic acid out of a racemic mixture. The formation of solid salts of R(+)-α-lipoic acid and arginine has been described for equimolar ratios only. DE 4317646 discloses the mixture of α-lipoic acid with alkaline compounds, including arginine, however in the compositions α-lipoic acid is present in excess.

None of these compositions would be suitable for the application in conditions of sexual dysfunction, because all of these compositions do not contain the combination partners in the appropriate amount and in the required ratio. The preparation of a composition as required for the intended use would also not work if prepared according to these descriptions. The proposed compositions would not be suitable for oral liquid intake.

Summing up, for the improvement of sexual function or treatment of sexual dysfunctions in both men and women a satisfactory therapy without the risk of severe side effects has not yet been provided. Consequently, there exist strong needs for a composition that can be applied without the risk of any severe side effect, which composition might be even applied as a dietary supplement, for improving sexual function in men as well as in women, which composition can also be useful as a medication for treatment of sexual dysfunction. Preferably, the composition should be suited for an easy application, most preferably via the oral route and even more preferably by intake of a liquid with a pleasant taste. Thus, a good the compliance of patients can be achieved, also for eledery patients. In particular for this group, usually in need of futher medications, the above mentioned medications (like PDE inhibittors) for improvement of sexual function should be avoided due to undesirable possible interactions of two or more medicaments.

Surprisingly, all above objects are solved by a composition comprising the combination of a NO donor or a precursor thereof, with arginine being a preferred compound, in combination with a dithiolane, with α-lipoic acid as a preferred compound, and its use for improvement of sexual function. The compositions according to the invention comprise the NO donor or its precursor in excess to the dithiolane on a molar ratio. As one example, the amount of arginine will exceed the amount of α-lipoic acid by a factor of 2.1-40, preferably 4-20 on a molar basis. The compositions are also suited for the effective treatment of the signs and symptoms of sexual dysfunction.

According to one embodiment, the present invention relates to the use of a dithiolane in combination with a NO donor or a precursor thereof for the preparation of a medication for treatment of sexual dysfunction.

NO donors or precursors or agonists for example are endothelin, cytokines, bradykinin, calreticulin, bisacodyl, phenolphthalein, organic nitrates and nitrites including volatile alkylnitrate preparations etc. α-Adrenergic blockers, like phentolamine, papaverine and prostaglandins are also in use. One preferred compound is arginine. Dithiolane compounds suited in the present invention are for example α-lipoic acid, β-lipoic acid, dihydro-lipoic acid, liponamide, bis- and tetranorlipoic acid, methyllipoic acid, 7,8-dithioheptanoic acid, 7,8-dithiononanoic acid and many others (see U.S. Pat. No. 6,387,945 B2, EP 089126 A1), with α-lipoic acid being preferred precursors, prodrugs and functional agonists of glutathione and can be used as well for this purpose.

For such compositions according to the invention the two components are arginine and α-lipoic acid, besides the prerequisite that the NO donor or its precursor (here: arginine) is present in excess, based on the molar amount of the dithiolane α-lipoic acid, preferably ranges for the amounts of the compounds present in the composition are from 200 mg to 15 g arginine and from 25 mg to 1.2 g of α-lipoic acid. Preferred amounts are between 500 mg to 10 g arginine and 55 mg to 800 mg α-lipoic acid, most preferred 3.5 g to 5 g arginine and 100 mg to 600 mg α-lipoic acid. For individual preparations the total intake of the two compounds and hence the respective ratio can be adjusted according to the respective needs, taking into consideration the pharmacokinetic and pharmacodynamic differences, conditions of the patients and individual co-medication and co-nutrition.

In general, the compositions according to the invention comprise at least a NO donor or precursor thereof (inducer of nitric oxide) and a dithiolane. Preferably, the NO-donor is the natural amino acid arginine as a precursor of NO-synthesis and the dithiolane the natural cofactor α-lipoic acid. More preferred, the biological "L"-form of arginine is used and the biological R(+)-enantiomer of α-lipoic acid. As to the claimed uses according to the invention, the two compounds "NO donor or precursor thereof" and "dithiolane" can be present in separate compositions as long as the intake for improvement of sexual function appears in combination of the two substances. As to the new uses according to the invention, the intake from separate compositions can be beneficial in such cases an individual dose adjustment of the two combination partners is required for the individually intended use.

According to a preferred embodiment, the compositions of the invention are to be applied orally. A preferred dose regimen is once a day, but an individually adjusted split of the daily intake over the day in more than one dosage may be beneficial.

Usually, pharmaceutically acceptable organic or anorganic salt partners have to be added due to the lower amount of dithiolane in the composition as compared to the NO donor or its precursor, in particular arginine. Such salts are in particular needed in liquid formulations, because both arginine and α-lipoic acid have a very limited solulability. Salt formation is required to achieve the required concentrations of the active partners particularly in a liquid formulation. However, the same holds true for solid oral formulations, if a complete and reproducible intestinal dissolution is required. Preferably, organic acids can be used as salt partners for the surplus of arginine, such as for example aspartic acid, glutamic acid, pyruvate, benzoic acid, lactic acid, citric acid, malonic acid, tartaric acid or polyanions or carboxylic acids in general. Preferably, the additional salt partner for the surplus of arginine should be an acid stronger than α-lipoic acid ($pK_a$ 5.3), for example ascorbic acid, malonic acid, citric acid and others. This provides benefits for a liquid composition, as the required high concentration of the active compounds in a solution can achieved more easily. The extremely bad taste of α-lipoic acid is usually prohibitive for its oral intake from a liquid presentation, however within the proposed compositions, oral application of a liquid composition is possible. It provides also benefits for a solid composition, preferably suited for oral intake, as the solulability of the active salt partners after ingestion is increased. In respect of taste it can be of some benefit for a composition to have the additional acid in a slight surplus in addition to the amount needed to compensate for the alkaline surplus of arginine. For stability reasons however, compositions with a higher amount of lipoic acid (like 100 mg and more) can be better formulated with a slight surplus of alkaline components. This surplus can be achieved either by arginine or even better by an additional alkaline component, preferably with a higher $pK_b$, as ethanolamine or tromethamine or organic alkaline compounds have.

A solid matrix or colloid-disperse gel polyionic matrix can be used for a solid form to be dispersed. Alternatively, a matrix as a colloid-disperse sol for a liquid form is suited. The compositions according to the invention may be in a controlled release state. The skilled person will chose in accordance with known pharmaceutical practice suited excipients to achieve standardized dosage forms.

Besides the two components discussed according to this invention, still further suited compounds as for example vitamins and minerals, metabolic intermediates, carbohydrates, lipids, fatty acids, alcohols, amino acids and peptides for pharmaceutical or pharmacological or nutritive usage or compounds for improving taste or smell, can be added.

For solid oral dosage forms, the total weight of a single dosage is in a range that allows easy swallowing. This can result in the intake of multiple units at once or over the day. With liquid tonics or effervescent compositions for being solved, the total daily intake can be achieved with one single unit easily. The solid is suited to become liquid prior to swallowing and is preferably rapidly disintegrating in the mouth.

The consumption of the liquid presentation can be facilitated by addition of sweeteners and flavors and colorants. Preferably, one dosage is presented in one unit. Most preferred, both compounds (NO donor and dithiolane) are presented in one dosage unit in a fixed ratio. Prepackaging would allow an individual dosing composition at the site of distribution. An example for a liquid composition may contain 10 g R(+)-alpha-lipoic acid as the dithiolane compound, 300 g of arginine as the NO donor compound, 199.5 g aspartic acid as additional anionic salt partner. The compounds will be dissolved under stirring together with 2% saccharose in a mixture of water/ethanol 95/5 w/w with a total volume of 5 L, sterilized for injection and filtered through a membrane filter with pores of 0.2 μm. 50 ml portions will be filled in drinking ampoules under aseptic conditions.

In the compositions of the invention it might appear that the two compounds are chemically bound together by other chemical bonds than ion bonds. For this purpose, both active partners can be linked by a functional spacer, which binds both partners via their chemically active moieties, for example via amide bonds, ester-, thioester- or ether bonds.

The invention also provides pharmaceutical or nutritive packages comprising one or more of the respective dosage forms according to the invention. The packages can be associated with a notice by a governmental or public agency which regulates and reflects manufacturing, distribution, promotion, storage or use of pharmaceutical, biological or nutritive products. The package can also contain a notice which declares the contents and the composition of the package, the stability and the methods of application and conditions of dosing and intake and purpose of use. The notices can either be added on a leaflet or can be printed on the packaging material.

With the compositions according to the present invention, for the first time an improvement of erectile function by making use of naturally occurring compounds has been observed, normalizing the function in most cases. The combination of the NO donor and the dithiolane in the proposed amounts and ratios is effective in cases of erectile dysfunction in which even high doses of arginine or of α-lipoic acid alone do not provide a treatment effect. Therefore, the effect of the proposed combination on erectile dysfunction can be considered as synergistic and can not be attributed to a lowering of arginine dependent side-effects by the thiol. Most surprisingly the observed effect is not limited to physical erectile dysfunction, but is also observed in cases of diagnosed psychogenic erectile dysfunction and on signs and symptoms of sexual dysfunction other than ED like diminished or absent libido, poor or absent ability to experience orgasm, decreased or absent salivation, reduced or absent clitoral erection and excitability and reduced labial and vaginal engorgement. This is remarkable, as the contribution of arginine to an effect on sexual function is known to be based on NO metabolism. Hence, any potential combinatory effect should be restricted to physical erectile dysfunction. Surprisingly, as described before, the effect of the combination of an NO donor and a dithiolane is not restricted to an NO-dependent pharmacology. Such observation overcomes a prejudice in the art. It is thought, although the present invention is not restricted to such an assumption, that the interactive action of the composition according to the invention has to be partly independent from an effect on nitric oxide metabolism. Such an assumption is supported by the observation that in addition to erectile function, sexual function was improved in general, including libido, both in male and in female. Although the mechanism of the observed clinical effects of the compositions is not yet completely understood, the positive effects appear to be based on the described ratio of the two compounds, which are preferably arginine and α-lipoic acid, with arginine in surplus.

It should be noted that with the composition according to the invention ED can be effectively treated in cases treatment with PDE5-inhibitors fails.

In particular, the invention relates to:

A composition comprising a NO donor or a precursor thereof and a dithiolane wherein the NO donor or it's precursor is present in excess based on the molar ratios.

A composition as stated before, wherein the NO donor or its precursor is arginine and the dithiolane is an α-lipoic acid derivative.

A composition as stated before, wherein the α-lipoic acid derivative is α-lipoic acid.

A composition as stated before, wherein a further acid is added, which acid is preferably pharmaceutical acceptable like L-aspartic acid, L-glutaminic acid, pyruvate, lactic acid, benzoic acid, malonic acid, citric acid, ascorbic acid and others.

A composition as stated before wherein chemical derivatives of α-lipoic acid and/or arginine are used like salts, esters, amides, ethers and other chemical derivatives, wherein the derivative is formed by chemical bonds either directly or via a conjugating moiety.

A composition as stated before useful as a drug, medical food, food supplement, nutraceutical or food.

A composition as stated before in liquid form, comprising additional anionic salt partners other than α-lipoic acid as counter ion for the NO donor or its precursor, which is preferable arginine.

A composition as stated before in liquid form for oral intake, comprising additional anionic salt partners other than α-lipoic acid as counter ion for the NO donor or its precursor, which is preferable arginine.

A composition as stated before in solid, comprising additional anionic salt partners other than α-lipoic acid as counter ion for the NO donor or its precursor, which is preferable arginine.

A packaged dosage form comprising the before described composition either in solid or liquid form.

A package dosage form comprising two separate dosage units, which—if taken together,—lead to the intake of a composition as described herein. In one of the units the additional salt partner may be added.

The use of a composition as described herein for improvement of sexual function.

The use of a composition as described herein for improvement of sexual function in males.

The use of a composition as described herein for improvement of sexual function in females.

The use of a composition as described herein, wherein the sexual dysfunction is a erectile dysfunction.

The use of a composition as described herein, wherein the sexual dysfunction is a psychogenic erectile dysfunction.

The use of a composition as described herein, wherein the sexual dysfunction is a physical erectile dysfunction.

The use of a composition as described herein, wherein sexual dysfunction is loss of libido in man.

The use of a composition as described herein, wherein the sexual dysfunction is loss of libido in women.

The use of a composition as described herein, wherein the sexual dysfunction is a based on a physical reason.

The use of a composition as described herein, wherein the sexual dysfunction is a based on a psychogenic reason.

The use of a composition as described herein, wherein the sexual dysfunction is frigidity, disability to achieve orgasm, ejaculatio praecox unacceptable short duration of intercourse, absent salivation, reduced or absent clitoral erection or excitability and reduced labial and vaginal engorgement.

The use of a composition as described herein for the preparation of a medication for the treatment of a sexual dysfunction.

Use for the treatment as stated before, wherein the sexual dysfunction is an erectile dysfunction.

Use for the treatment as stated before, wherein the sexual dysfunction is loss of libido in either man or women.

Use for the treatment as stated before, wherein the sexual dysfunction is based on physical reasons.

Use for the treatment as stated before, wherein the sexual dysfunction is frigidity.

Use for the treatment as stated before, wherein frigidity results in disability to achieve orgasm.

Use for the treatment as stated before, wherein the sexual dysfunction is a based on psychogenic reasons.

Use for the treatment as stated before in males.

Use for the treatment as stated before in females.

Use for the treatment as stated before, wherein the sexual dysfunction is ejaculatio praecox.

Use for the treatment as stated before, wherein ejaculatio praecox results in unacceptable short duration of intercourse.

Use as stated before wherein α-lipoic acid and arginine or related compounds are taken orally or parenterally, either in a solid or liquid presentation form.

Use as stated before wherein α-lipoic acid is used as enantiomer (R(+) or S(−)) or as a mixtures of the enantiomers, including a racemic mixture.

Use as stated before wherein arginine is used as the L- or D-isomer or a mixture of both.

Use as stated before wherein the dose of a medication for a basis therapy of erectile dysfunction can be reduced. The basis medication can be a PDE5-inhibitor, a blood flow enhancer, a stimulator of erection, a hormonal replacement therapy.

Use of a composition as described herein for the preparation of a medication for the treatment of a sexual dysfunction while simultaneously reducing the dosage of a medication for treatment of erectile dysfunction for avoiding adverse side effects appearing with the basis medication.

The use of a composition or both components together as described herein in addition to a basic intake of alkylnitrates, such as volatile alkylnitrates or other sexual stimulators.

PHARMACEUTICAL EXAMPLES

The following examples 1-4 show typical compositions according to the present invention. When preparing the compositions, it is of advantage to directly solve salts of lipoic acid or arginine instead of the free acid or base, particularly in case of the natural form. The ratio of surplus of arginine contributes to stability and acceptable taste. The water should be preferentially at 10° C., sterilised and degassed. Antioxidants like ascorbic acid are helpful to improve stability and can improve taste. Off-flavours contribute to cover remaining traces of bad odour. Complex carbohydrates of synthetic or biological origin contribute to protect against bad taste.

The following examples are only special embodiments and do not limit the scope of the present invention.

Example 1

| | |
|---|---|
| α-lipoic acid choline | 1.58 g |
| L-arginine | 25 g |
| β-Cyclodextrine (Cavamax ® W7) | 16.5 g |
| ascorbic acid | 1 g |
| rum aroma | 100 μL |
| citric acid | ad pH 6.8 |
| water | ad 1000 mL |
| carbon dioxide | ad saturation 1.2 bar | packaged in PET bottles 200 mL and stored at 4° C.

Example 2

| | |
|---|---|
| R(+)-α-lipoic acid tromethamine | 3.18 g |
| L-arginine | 12.5 g |
| β-Cyclodextrine (Cavasol ® W7) | 33.5 g |
| ascorbic acid | 1 g |
| vacilla aroma | 200 μL |
| citric acid | ad pH 7.8 |
| water | ad 1000 mL | packaged in PET bottles 200 mL and stored at 4° C.

Example 3

| | |
|---|---|
| α-lipoic acid | 1 g |
| choline | 0.58 g |
| L-arginine | 25 g |
| honey pasteurised | 50 g |
| ascorbic acid | 1 g |
| citric acid | ad pH 7.8 |
| water | ad 1000 mL | packaged in PET bottles 200 mL and stored at 4° C.

Example 4

| | |
|---|---|
| α-lipoic acid arginine | 3.7 g |
| L-arginine | 12.5 g |
| β-Cyclodextrine (Cavasol ® W7) | 16.5 g |
| raspberry aroma | 300 μg |
| citric acid | 23 g |
| NaHCO$_3$ | 10 g | packaged in 5 sachets or pressed in 5 effervescent tablets

Clinical Examples

Case 1

A male of 37 years suffered since 3 months from worsening of erection (reduction of penile tension) and of a slight reduction of libido. His IIEF count at the examination was 9. All biochemical parameters and hormones were within the normal range. The Doppler sonography of the penile vessels was normal. A challenge test with Silfenadil was positive, thereby excluding an organic pathology of the erectile dysfunction (ED). Administration of Silfenadil evoked severe redness of face, creating discomfort feeling to the patient. Psychogenic ED was diagnosed after examination. Oral intake of 600 mg α-lipoic acid did not change the IIEF score. Arginine (5 g) and 600 mg α-lipoic acid were taken orally 30 minutes prior intercourse. After therapy, erection normalized. The IIEF score improved from 9 to 21 points.

Case 2

A male of 23 years complained since a week about insufficient erection. The man started sexual life at the age of 18 with regularly intercourse twice a week. 3 months ago, he changed the sexual partner. At the $1^{st}$ intercourse with the new partner, he experienced overexcitement. Since that time erection worsened, with an IIEF score of 8 points. The biochemical and hormonal values were within the normal range. The diagnosis was psychogenic ED and failure expectation syndrome. Oral intake of 4 g arginine did not change the IIEF score. Also intake of 1 g arginine together with 600 mg α-lipoic acid 30 minutes prior intercourse did not result in any improvement. After change to 4 g arginine and 300 mg α-lipoic acid, the erection improved. The IIEF score improved from 8 to 12 points. In the meantime, the patient changed to chronic intake of 1 g arginine+100 mg α-lipoic acid daily. Occasionally, he takes on demand prior intercourse additional 4 g arginine+300 mg α-lipoic acid.

Case 3

A male patient of 35 years complained about worsening of erection since 7 years. Sexual intercourse was only possible in selected position. In addition, he suffered from premature ejaculation. His libido remained intact. The IEFF score at diagnosis was 11. The diagnosis was physical ED and premature ejaculation. 600 mg α-lipoic acid was given as single dose and arginine was given in 4 single doses over the day of 2 g. The erection improved and the intercourse was prolonged from 1-2 minutes to 7 minutes. The IEFF score changed from 11 to 15 points. The 4 single doses have been changed to a single dose of 10 g arginine, taken together with the α-lipoic acid.

Case 4

A 44 year old patient (company manager with associated psychological stress) complained about reduced erection and reduced libido since the last 13 years. The morning reactions retained. Sexual contacts had a frequency from 3 times a week ago to 3 times a month. The diagnosis was psychogenic ED and manager syndrome. A single dose administration of 200 mg α-lipoic acid was without any effect and an increase to 600 mg did improve the situation. However, 200 mg α-lipoic acid together with 5 g arginine fully normalized erection. The IIEF score improved from 9 to 24 points. For chronic intake, the daily dose of arginine has been reduced to 2 g, with no change of the α-lipoic acid intake.

Case 5

A 37 year old patient complained about worsening of erection and premature ejaculation. After administration of Silfenadil and Verdenafil, the erection improved; however, the premature ejaculations remained. The diagnosis was psychogenic ED and premature ejaculation. On-top to this basic treatment, 10 g arginine were administered, without any effect. However, 200 mg thioctic acid together with 10 g arginine led to an improvement of the IIEF from 8 to 20 points. The duration of intercourse was extended from 1 to 4 minutes.

Case 6

A women of 32 years experienced loss of libido after she has born her first child. Intercourse was often painful due to diminished salivation. She did not experience any orgasm since she felt the absence of libido. Since two years, she regularly attends with her husband marriage counseling. She started with an intake of 3 g of arginine daily and increased to 10 g, which did not improve the situation. α-lipoic acid was added, starting with 100 mg daily. The dose was increased weekly by 100 mg. After receiving 300 mg α-lipoic acid, she reported the $1^{st}$ sensation of libido. She takes now 300 g α-lipoic acid and 5 g arginine together and has regained the ability to achieve orgasms regularly. The ISFS questionnaire improved (10 points). She reported that her partnership has improved. Marriage counseling has been aborted.

Case 7

A 55 year old man was able to perform intercourse only after nasal intake of isoamylnitrite since 5 years. However, intercourse was still unsatisfactory due to unpredictable erections and premature ejaculations. The diagnosis was physical erectile dysfunction and premature ejaculation. After introduction of intake of 10 g arginine and 600 mg α-lipoic acid, the typical duration of intercourse could be prolonged from 2 minutes to 5 minutes and the dose of amyl-nitrite could be reduced. During chronic intake of arginine+α-lipoic acid, the intake of the combination was reduced to 5 g+300 mg. The intake of isoamylnitrate is not required anymore.

None of the cases reported adverse events due to the intake of the combination partners. Attributes of cardiovascular dysfunction were not observed. Acutely, oral liquid presentations were applied, chronically both liquid and solid presentations.

The combination is effective in signs and symptoms of erectile dysfunction, but not limited to physical (organic) erectile dysfunction. Other attributes of sexual function and libido are also improved, both in men and women. In conclusion, the intake of the combination provides treatment effects that include effects as mediated by nitric oxide but are not limited to a nitric oxide dependent pharmacology.

The invention claimed is:

1. A liquid composition comprising: arginine, and α-lipoic acid in an amount of up to 1.2 g, wherein the arginine exceeds the amount of the α-lipoic acid on a molar basis by a factor of 2.1 to 50, the composition being suitable for oral administration as a liquid, and the α-lipoic acid is R-α-lipoic acid.

2. The composition according to claim 1, wherein the amount of the arginine exceeds the amount of the R-α-lipoic acid by a factor of 4 to 20.

3. The composition according to claim 1, wherein the excess of arginine in relation to the R-α-lipoic acid is compensated by additional anionic salts.

4. The composition according to claim 1, wherein the amount of arginine is from 200 mg to 15 g and the amount of α-lipoic acid is from 25 mg to 1.2 g.

5. The composition according to claim 4, wherein the amount of arginine is from 500 mg to 10 g and the amount of α-lipoic acid is from 55 mg to 800 mg.

6. The composition according to claim 5, wherein the amount of arginine is from 3.5 g to 5 g and the amount of α-lipoic acid is from 100 mg to 600 mg.

7. The composition according to claim 1, wherein the arginine is L-arginine.

8. The composition according to claim 1, further comprising ascorbic acid as an antioxidant.

9. The composition according to claim 1, further comprising at least one complex carbohydrate.

* * * * *